United States Patent [19]
Klein et al.

[11] 3,989,463
[45] Nov. 2, 1976

[54] SENSING ELEMENT AND DETECTION SYSTEM EMPLOYING SUCH ELEMENT FOR DETECTION OF ENVIRONMENTAL BORNE MATERIAL

[75] Inventors: Carl F. Klein, Milwaukee; Paul E. Thoma, Burlington, both of Wis.; Gerald E. Weber, Ben Brook, Tex.

[73] Assignee: Johnson Controls, Inc., Milwaukee, Wis.

[22] Filed: Aug. 26, 1975

[21] Appl. No.: 607,892

Related U.S. Application Data

[63] Continuation-in-part of Ser. No. 445,488, Feb. 25, 1974, abandoned.

[52] U.S. Cl. .................................. 23/254 E; 73/23; 317/246; 317/249 R; 317/258; 340/237 R
[51] Int. Cl.² .................. G01N 27/00; G01N 31/00; G08B 21/00; H01G 5/00
[58] Field of Search .......... 23/254 E, 255 E, 232 E, 23/254 EF; 73/23; 340/237 R; 324/61 R, 61 US, 61 P; 317/246, 249 R, 258 (U.S. only)

[56] References Cited
UNITED STATES PATENTS

| | | | |
|---|---|---|---|
| 2,972,570 | 2/1961 | Haas et al. | 317/258 X |
| 3,255,389 | 6/1966 | Salomon et al. | 317/258 X |
| 3,483,451 | 12/1969 | Klerer | 317/258 |
| 3,495,142 | 2/1970 | Herrgen et al. | 317/249 R |
| 3,754,219 | 8/1973 | Klein | 340/237 R |
| 3,798,516 | 3/1974 | Short | 317/258 |

*Primary Examiner*—Joseph Scovronek
*Attorney, Agent, or Firm*—Andrus, Sceales, Starke & Sawall

[57] ABSTRACT

An air pollutant and/or fire combustion sensing apparatus includes a pair of sensing electrodes separated by a free space to define a capacitance unit. At least one of the electrodes includes a corrosion-resistant, conductive material which interacts with air borne products to alter the permittivity and/or charge transfer characteristic of the unit. The material is in the form of a highly corrosion-resistant metal selected from a metal or metal alloy including at least one of the metals selected from the Group VIII, periods 4, 5, and 6 of the periodic table, particularly rhodium and stainless steel. Carbon and copper respond to produce a detectible output. An amplifying and alarm circuit is connected to the capacitance unit, and responds to either an increase or a decrease in the capacitance as a result of the interaction with the sensing electrode material. The circuit includes a thermally stabilized field effect transistor as a buffer input amplifier connected in differential configuration to produce a high input impedance and a high gain. The transistor is connected to a high gain DC operational amplifier having a feedback compensation network to compensate for thermal and low frequency drift change. A constant current source provides the bias supply to the input amplifier to improve common mode rejection and the thermal stability. A pair of programmable unijunction transistors are connected to the output of the operational amplifier and to the input of an alarm device to detect either an increase or a decrease at the amplifier output which may arise as a result of the decreased or increased capacitance characteristics of the air borne material.

25 Claims, 5 Drawing Figures

U.S. Patent  Nov. 2, 1976  3,989,463
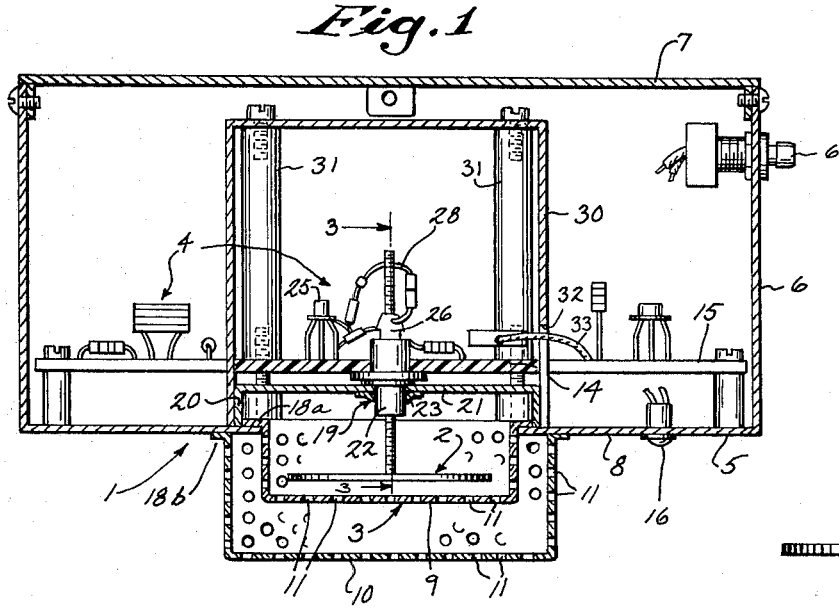

SENSING ELEMENT AND DETECTION SYSTEM EMPLOYING SUCH ELEMENT FOR DETECTION OF ENVIRONMENTAL BORNE MATERIAL

BACKGROUND OF THE INVENTION

This application is a continuation in part of applicants' application entitled Sensing Element and Detection System Employing Such Element for Detection of Environmental Borne Material, which was filed on Feb. 25, 1974 with Ser. No. 445, 488, now abandoned and further includes subject matter originally claimed and cancelled from the above entitled application.

This invention relates to a gaseous product detection system and particularly to an improved capacitance sensing element for such a system for detecting environmental borne particles such as generated, for example, as a result of air pollution, solvent evaporation, combustion or the like.

Combustion detection and alarm systems employing various sensing and detecting means have been suggested, such as thermal, flame, photo-electric, ionization chamber, semiconductors of a metal oxide or a polymeric organic material and electrolyte cell sensors. Capacitance sensing units have also been suggested. The inability to sense combustion at the initial or incipient stage, as contrasted to a more advanced stage, has severely limited the application of prior art devices employing photoelectric, flame and thermal responses because they do not react to the invisible combustion gases associated with the incipient stage. Ionization chamber sensors which respond to the physical and chemical composition of the atmosphere have, therefore, been relatively widely employed. The latter sensors, however, generally employ radioactive alpha particle sources and generally require special dual chamber constructions for reliable response. The development of high input impedance solid state devices and particularly field effect transistors has permitted substantial simplification in the circuits for ionization chamber sensing devices as well as capacitance sensors and has also permitted reliable designs. A further approach to a sensing unit is disclosed in the copending application of Carl F. Klein entitled "HIGH IMPEDANCE GASEOUS ION SENSING AND DETECTION SYSTEM", filed on Jan. 3, 1972, with Ser. No. 214,884, which issued as U.S. Pat. No. 3,754,219 on Aug. 21, 1973 and which is assigned to the same assignee as the subject application. In the latter system, a sensing head includes a static charge sensing electrode mounted within a chamber defined at least in part by a referenced electrostatic perforated shield which permits free movement of the surrounding environment into the chamber. The charge gradient on the sensing electrode changes, either due to a direct or induced charge transfer, in accordance with the ions and charged particles in the environment between the plates. This provides a capacitance signal related to the interelectrode space environment which is detected by high impedance devices connected to the sensing electrode, such as field effect transistors which is preferably a dual MOS-FET transistor operating in its active region or any other similar high impedance device. The sensing electrode is mounted with a high bulk and surface resistivity insulator to prevent charge leakage within a dome-shaped and perforated ground shield. The change in the sensor's charge gradient can be either positive or negative and, the sensing circuitry responds to both the positive and negative changes in the quiescent charge condition.

The characteristic of the sensing head is responsive to contaminating charged ions in the surrounding gaseous environment which enter through the perforated outer electrode. Environmental borne gaseous ions such as those associated with combustion carry a distinct electrical charge. Although incipient combustion products will normally generate electrically charged products, the surrounding environmental ions normally present will tend to neutralize the generated charges. It is, generally, only when an unusually significant charge generation such as associated with an advanced stage of combustion arises that a conventional electrostatic sensor provides a highly significant response.

Other systems have also recently been suggested to overcome the objection to ionization chambers and the like. For example, certain metal oxide semiconductors, when heated to a relatively high temperature, may also provide a variable resistive detection means as shown in U.S. Pat. No. 3,603,954. An electrolytic cell unit is disclosed in U.S. Pat. No. 3,755,800 wherein the products of combustion react with an anodic powered electrode and a special interelectrode electrolyte to produce a controlled current flow which can be used to drive a current responsive alarm. Although such systems avoid certain problems associated with ionization chambers, they do have special constructional and operational limitations. The heating of the metal oxide semiconductor to the desired temperature requires a significant power and stresses associated with expansion and contraction may cause the heater coil-electrode to separate from the semiconductor and malfunction. In an electrolytic unit, an electrolyte must not only be provided but must be maintained.

Although many different approaches and suggestions do appear in the prior art, there remains a need for a simple, reliable and long life sensing element to detect environmental borne products and particularly combustion products at the incipient stage of combustion.

SUMMARY OF PRESENT INVENTION

In accordance with the present invention, a capacitance sensing element having a free space is exposed to the environment and the permitivity or capacitance is directly related to and responsive to a variety of airborne materials including the products of combustion at the incipient stage of combustion and generally materials with a high dielectric constant. Applicants have discovered, however, that if detection is made dependent not upon the provision of a special interelectrode dielectric as such, but rather upon particular reacting electrode surface materials, a highly practical and operable system is obtained. Applicants have particularly found that air pollution and the combustion products will specifically interact with selected conductive sensing materials which are characterized by being essentially corrosion free ro resistant to chemical oxidation, and which, therefore, prevent a creation of a non-reactive massive oxide layer on the surface of the sensing material.

Applicants have particularly found that the metals and alloys which include Group VIII elements in periods 4, 5, and 6 of the periodic table as well as carbon products provide high sensitivity to the contaminating products. Within this grouping, rhodium, platinum and palladium have been found to have optimum sensitivity to the gaseous products of combustion and to retain high sensitivity levels for an indefinite period. Alloys containing at least 5% by weight of a metal from the Group VIII elements may also be employed such as the iron and nickel alloy, and stainless steel particularly of the 300 series. Copper and brass have also been found to give high sensitivity. Copper and brass, however, have a shorter life due to greater oxidation. A silver palladium alloy has also been found to be quite sensitive. Carbon is quite sensitive but is a rather fragile sensing material. The reactive material selected may be alloyed (but should be at least 5% by weight reacting material) with any desired other material which preferably also has a high resistance to oxidation to prevent possible formation of a non-sensitive oxide layer. Thus, with the present invention, a highly significant increased sensitivity of sensing means is obtained by proper selection of the capacitor elements so as to enhance interaction between the contaminating products and the sensing means. The sensing electrode may be an integral element of the material alone or the corresponding sensing material may be deposited or clad onto a base conductor. A plated or clad layer only a few atoms thick will produce a highly sensitive electrode such as 25 micro-inches of rhodium on brass or stainless steel. Although the precise mechanism cannot be definitely stated, it appears the special element or means, and particularly the identified elements have the proper electronic structure to absorb the contaminating gaseous products and cause a change in the permittivity and/or charge transfer characteristic of the element as such without generating a massive oxide coating or layer. This results in a change in the capacitance of the sensing unit. The adsorption characteristic may be either the conventional physical or chemical action. Generally, physical absorption relates to an interacting attachment or bond between the product and sensing means based on Van der Waals' intermolecular forces. Chemical absorption on the other hand generally involves actual transfer of electrons and is similar to a chemical compound formation. Thus, the metals react with and bond with the combustion particles by a dispersion force and dipole type action. Any surface coating including alloys which have the appropriate element which is highly resistant to chemical oxidation so as not to develop a massive oxide layer will produce a sensitive detection to the products of combustion and the like. Although the precise range is not critical, an alloy should include at least 5% of a reactive element for practical implementation.

Although the charge variation associated with the present invention is significantly greater than that heretofore suggested in the prior art, the magnitude of the change remains small and requires a high input impedance device which also has good electrometer characteristics. The capacitance sensor of this invention is, therefore, connected to a high impedance input means which is preferably constructed with a paralleled diode impedance element and which is also responsive to either an increase or decrease in the capacitance characteristic. In accordance with a further feature of the invention, the input means is a differential FET (field effect transistor) unit connected in a common mode rejection configuration and biased from a constant current source. The source may conveniently be a field effect transistor. Suitable operational amplifier units increase the signal level, with phase compensation to improve the stability of operation. The operational amplifier unit is also specially constructed with a single polarity power supply to simplify the design and minimize the power drawn by the sensing assembly. A pair of programmable unijunction transistors provide an exceptional satisfactory trigger circuit for actuating of a gated output switch such as a controlled rectifier means in response to either a positive or a negative voltage variation at the sensor capacitance meeans. The inputs are capacitively coupled to the amplifier unit to provide DC isolation and the circuit may be further provided with temperature stabilizing elements.

Further, the basic capacitance of the sensing unit as determined by the electrode spacing, although not critical, is significant. The electrodes are, therefore, in a best mode construction mounted to permit fine adjustment of the spacing. Further, shielding of the sensing electrode is another significant factor and Applicants have found that improved results are obtained, although not required, with a pair of perforated shielding electrodes mounted in overlying spaced relation to the sensing electrode.

More particularly, a highly practical construction includes a disc-like sensing electrode having a sensing surface of the special conductive material or an alloy thereof. A base electrode of stainless steel having a gold strike and plated with rhodium is a particularly practical novel construction. A threaded shaft is secured to the backside of the electrode and is mounted in special high bulk and surface resistivity support member to prevent loss of the small signals and with an electrical output connection to the shaft. The contact may be practically provided by a tubular clip within the support member. The mounting member is secured within an enclosure means including a special shielding member overlying the assembly with the sensing electrode. The shielding electrodes are suitably perforated to permit the free movement of the atmosphere into the sensing electrode and, in particular, into contact with the special noncorrosive reactive materials. The sensing electrode is coupled to the high impedance, high gain signal processing circuitry to provide a compact, integrated detection head.

The present invention has been found to provide a highly sensitive surface sensing element for sensing of products of combustion and like environmentally borne products without the necessity for special interelectrode materials being provided as a result of the novel discovery of the importance of the surface interaction.

BRIEF DESCRIPTION OF THE DRAWING

The drawing furnished herewith illustrates a preferred construction of the present invention in which the above advantages and features are clearly disclosed as well as others which will be clear from the following description of such embodiments.

In the drawing:

FIG. 1 is a vertical sectional view of a sensing unit constructed in accordance with the present invention;

FIG. 2 is a bottom elevational view of FIG. 1 with parts broken away and sectioned to show details of construction;

FIG. 3 is an enlarged view taken generally on line 3—3 of FIG. 1;

FIG. 4 is an enlarged fragmentary sectional view of an electrode unit shown in FIGS. 1 - 3; and FIG. 5 is a schematic circuit diagram of a fire detection apparatus incorporating the sensing means of the present invention.

DESCRIPTION OF THE ILLUSTRATED EMBODIMENTS

Referring to the drawing and, in particular to FIGS. 1–3, a sensing head 1 having a special reactive sensing electrode 2 constructed in accordance with the teaching of the present invention is shown. An integrated head 1 is illustrated with a capacitance unit 3 connected to a high impedance signal processing circuit 4, such as shown in FIG. 5, with a single enclosure 5.

The sensing head 1 and particularly enclosure 5 includes an outer supporting housing or case 6 having a removable back wall 7. The front wall 8 is provided with a center opening through which the sensing electrode 2 is mounted, and with a pair of cup-shaped perforated sensing capacitor plates or electrodes 9 and 10 mounted to the front wall and projecting outwardly therefrom in spaced overlying relationship to electrode 2. Perforations 11 in both of the shielding electrodes 9 and 10 permit essentially free access of the surrounding environment into the interior of the electrodes and into contact with the special electrode 2.

In accordance with the illustrated embodiment of FIGS. 1 and 2, the electrode 2 is a disc-like element including a base metal 12 and a special reactive material 13 located in spaced opposing relation to the inner shielding electrode 9.

The electrode coating or layers 13 is a corrosion resistant and conductive material which for optimum and practical sensing is selected from a particular metal group or an alloy of such group which Applicants have found interacts with and captures combustion and/or pollutant type products to produce a detectable electrical signal. In particular, for combustion detection, Applicants have found that the reactive material must be an essentially noncorrosive or corrosive resistant such as to prevent formation of a massive non-reactive surface as a result of reaction with the surrounding atmosphere. Further, not all materials similarly interact and the sensitivity of the sensor is dependent upon the particular surface material; and the metals of Group VIII, as set forth in *General Chemistry* by Nebergall & Schmidt, 1959 Ed., by D. C. Heath & Co., of Boston, Mass., as well as copper and carbon have been found to be unusually responsive. Of the Group VIII metals, those in periods 4, 5, and 6 and particularly rhodium, ruthenium, palladium and platinum provide significant detection capability with long term stability of operation and structural characteristic adapted to practical construction and use. Alloys of this group of metals will also provide highly satisfactory results. For example, a 300 series stainless steel has been employed with highly practical results. Stainless steel also provides a particularly economical sensing material. Silver palladium alloy also provides a satisfactory sensitivity. Carbon including graphite has the desired sensitivity and long term stability of operation but is generally physically fragile and thus difficult to construct and subject to damage in use. In contrast, copper and brass provide the desired combustion sinsitivity but brass and copper are somewhat unstable and after a period of time in the atmosphere, the sensitivity may become practically nil. Similarly, the sensitivity of nickel degrades. A nickel surface may operate for two or three months. Such material could, therefore, only be employed in very special cases to respond within a short period of time after exposure to a given atmosphere. Gold on the other hand, was also tried and was found to have a limited sensitivity to combustion and pollutant products. Iron and cobalt oxidize rapidly and have a relatively short effective life.

Although the precise surface mechanism is not completely understood, the electron configuration and the various adsorptive characteristics of certain of the materials appear to contribute to enhancement of the total response of the sensor. This would also explain the significance of the corrosion resistant quality. Thus, any massive oxide or similar coating as a result of sulfur, chlorine, or similar environmental elements destroys the response. Platinum group metals of Group VIII which include ruthenium (Ru), rhodium (Rh), palladium (Pd), osmium (Os), iridium (Ir), and platinum (Pt), all have similar electronic subshells. The d-band orbit of shell N of Ru, Rh and Pd, and of shell O of Os, Ir and Pt are not completely filled, and each band has at least one electron, and doubling up of electrons in each of the five orbitals occurs. These common characteristics which produce a resistance to any massive oxide formation appear to be significant in the long term, unchanging sensitivity to the products of combustion.

The present invention thus teaches that a highly significant result is obtained by the use of a proper surface of a conductive sensing electrode wherein the changes are the direct result of the interaction between the pollutant products and the surface material. Further, an essential teaching is that such surface provides a reliable, long operating, life if the surfaces are corrosive resistant, which, for the purposes of the present invention, is employed to define a material which reacts to form a minute layer but will not react with the surrounding normal atmosphere to develop a non-reactive protective layer. Thus, gold, which does not react to form an oxidized layer and also has good surface conductivity, would normally have been expected to produce a highly satisfactory and long life material. However, in fact, gold has less sensitivity than the platinum group metal. This apparently arises because of the complete lack of reactivity to the surrounding environment, whereas the metals which have greater sensivity have a thin oxide layer. Generally, the materials of Group 8 and alloys including such materials may form a reactive layer on the order of one microinch. However, significantly greater reactive layers which are less than 1000 micro-inches may provide some response, with the sensitivity degrading with the heavy layers. Any greater thickness of the reactive layer is generally a massive oxide layer and essentially prevents detection of the environmental borne element.

In summary, the special reactive material appears to have reaction with the various combustion type products including the gaseous ions, free radicals, charged particles and aerosols as well as high dielectric constant vapors. The ionic and charged particles appear to react directly with the reactive metal to obtain a charge transfer and a corresponding change in the probe output. The high dielectric constant vapors appear to be adsorbed by the probes surface, with a resulting change in the charge transfer characteristic and the probe output.

The characteristic of the capacitance element so formed is unusually and extremely sensitive to the environmental borne contaminating products such as the pollutants and combustion products. Although the charge levels are very small such as of the order of $10^{-4}$ to $10^{-2}$ volts, they can be readily detected with a proper high input impedance solid state type circuitry, as shown in FIG. 5.

The electronic components of processing circuit 4 are shown specially mounted upon a pair of suitable circuit boards 14 and 15 within the enclosure 5 and connected to actuate an alarm, such as a light emitting diode 16 mounted in an outer side wall to form the integrated compact sensing head. The electrode 2 is supported on the board 14 by a stem 17.

The enclosure 5 is mounted within the environmental space or area within which the pollutant products are to be detected, with the openings allowing relatively free movement of the surrounding environment around the electrodes and in particular between the electrodes 2 and 9 and particularly about the special electrode material 13. The process of combustion generates invisible products which, however, rapidly disperse within the enclosed area such as a room. Entry of such products within the sensing chamber interact with the sensing electrode 2 and particularly the special reaction material 13 to generate an electrical signal which, although of a generally minute level, may be reliably detected by a circuit 4 employing present day technology to establish reliable detection of the incipient stages of combustion. Thus, the change in permittivity or charge transfer character of the sensing electrode results in a voltage signal developed across the electrodes and is applied to a high input impedance circuit such as shown in FIG. 5 and presently described.

The capacitance sensing electrode of the present invention can be formed as illustrated in FIG. 4 with a coated electrode or may be constructed as a solid electrode of an appropriate conductor as long as the exposed surface characteristic provides for special interaction with the environmental borne products or aerosols which the capacitance unit is to detect. A satisfactory disc electrode includes a brass circular plate 12 and a brass stem 17 silver brazed to the plate 12 with brazing metal of Braze BT (72% Ag and 28% Cu). The base elements, and at least the outer circular plate portion, is given a thin, gold strike 18 over which one of the platinum group metals is placed to form reactive layers 13. The gold strike promotes the adhesion between the base metal and the probe material which is applied by plating upon the gold strike. Of the platinum group metals, rhodium, platinum and palladium plating solutions are readily available. Of these, rhodium has a slightly greater sensitivity to combustion products and, therefore, is preferred. Ruthenium plating solutions are not readily available and are easily contaminated. Osmium and iridium are not available in a aqueous plating solution but only in a molten cyanide bath and thus are not as acceptable as the aqueous plating solution metals. In an actual construction, as shown in FIG. 4, a 1.375 inch brass disc, which was 0.031 inches thick, was provided with a gold strike 18 of between 3 to 10 microinches and an outer reactive rhodium layer 13 between 25 to 500 microinches. The brass stem 17 was provided with a number 2–56 thread for mounting as shown in FIG. 1.

More particularly, the inner apertured or perforated electrode 9 is a cup-shaped, cylindrical conductor extended through the opening in wall 8 and having a circular flange 18a soldered or otherwise secured to the inner side of housing wall 8 to provide a common ground connection. Electrode 10 is similar to and slightly larger than electrode 9. Electrode 10 is mounted in telescoped, spaced relation to electrode 9 and has a mounting flange 18b similarly secured to the outer front wall 8. The disc electrode 2 is located within the inner shielding electrode 9 and is supported by the threaded shaft 17 which is integrally attached to the backside of the electrode. The shaft 17 projects into the enclosure and is supported on board 14 within a special bushing unit 19 formed of an ultra high surface and bulk resistivity material to isolate the capacitance sensing probe or electrode 2 from ground and maintain proper response and input to the electronic circuitry which is mounted within the housing on the circuit board 14. In the illustrated embodiment of the invention, a cup-shaped metal support 20 is disposed within the enclosure in overlying relationship to the shield electrode 9 and particularly flange 18. The base 21 of support 20 includes an opening to accommodate a plastic, flanged bushing 22 of unit 19 which is clamped in place by a small spring nut 23. The bushing 22 proejcts downwardly toward the electrode 2 about the shaft 17. A similar, oppositely disposed bushing 24 rests on the flange of bushing 22 and projects upwardly through an opening in the circuit board 14 which supports input amplifying components 25 of circuit 4 which is more fully described hereinafter. A tubular metal contact 26 is wedged within the bushing 24 with the shaft 17 supported therein. Thus the contact 26 includes a pair of spring arms 27 which resiliently grip the threaded shaft 17 to define a nut-like attachment and provide a firm electrical connection. Rotation of the shaft 17 provides for fine tuning or adjustment of the disc-like electrode 2 with respect to the shield electrode 9. A lead 28 connects the contact 26 to the input component of the signal processing circuitry. The provision of a very high resistance insulation between the probe 2 and the case or ground shield, such as provided by the bushing unit 19 is extremely important. If the bulk resistance is not high, leakage current will travel through or over the surface with resulting adverse detection operation. Similarly the insulator unit 19 must be kept clean and dry to prevent destruction of the desired insulating characteristic. Applicants have found that polyethylene and "Teflon" materials are exceptionally well suited. The bulk resistivity is in excess of $10^{16}$ ohm cm and water vapor films and the like do not form readily on such materials. "Teflon" has a slightly greater surface resistivity because it is more resistant to water vapor adsorption. The contact and associated amplifying components carried by the insulating circuit board 14 are enclosed by a cup-shaped shield member 30 formed of brass or the like and secured within the enclosure. The shield member 30 functions to isolate the amplifying circuit from any external charge or field which, because of the minute energy levels involved in the novel detection process, could cause spurious response. The cup-shaped member 30 is a solid wall member which is bolted or otherwise secured in abutting relation to the front wall of the enclosure 5 by suitable supporting posts 31 to essentially, totally enclose the components and electrode connection. A small, edge notch 32 is provided for the input-output leads 33 of the circuitry carried by the insulating board 14. The second circuit board 15 is supported within the enclosure 5 to one side of the shield 30 adjacent the lead slot 32. The power amplifying and triggering portion of the processing circuitry is supported on board 15. The input is connected to the leads 33 and the output is connected to energize the lamp 16 in the presence of the products of combustion.

The electronic processing circuit 4 may, of course, be of any suitable construction adapted to provide a high impedance input connection to the electrodes 2 and 9 so as to reliably detect the relatively minute changes which are involved in the detection process. A particularly satisfactory circuit is shown in FIG. 5.

Referring to FIG. 5, lead 28 connects the terminal 26 as the input to a buffer amplifying stage 34 with a high value resistance branch 35 connected in parallel with the sensing head 1. The branch 35 includes a field effect transistor 35a having a Zener gate input connected in series with a resistor such as disclosed in U.S. Pat. No. 3,754,219 to Carl F. Klein. The branch 35 acts as a bleed resistance which prevents the gradual accumulation of charge on the capacitor of sensing head 1 and particularly capacitance element 3 with time and thereby maintains reliable detection. The transistor 35a provides a very high impedance with essentially no noise generated signals and with good thermal stability. This is in contrast to employing of a carbon resistor or the like which are relatively electrically noisy and have relatively poor thermal stability.

The transistor 35a is also a very rugged unit and is not subjected to mechanical or physical destruction as a result of mechanical shock loads such as encountered with the more conventional higher kilomegohm resistances which can, of course, within the broadest concept of the present invention, be employed. If such resistance elements are employed special care should, of course, then be taken in connection with the application of the device to prevent the adverse effects associated with mechanical shock and the like.

The buffer amplifying stage 34 is shown as a dual field effect transistor unit including a pair of FET transistors 36 connected in a differential amplifier configuration to provide a common mode rejection of extraneous signals and operating in a single ended output mode. The FET amplifier also has low noise characteristics and good thermal stability. Although any suitable high impedance device or circuit can be employed, the MOS-FET transistor unit is particularly adapted to this application because of its very high input impedance, of the order of $1.0 \times 10^{16}$ ohms, and its ability to detect a very small voltage variation. The dual field effect transistor amplifier stage is also driven from a constant current source shown as a field effect transistor 37 having the source and drain connecting in common with the two transistors 36a of the stage 34. A potentiometer 38 is connected in series with transistor 37 to the bias supply to establish an adjustable constant current supply.

The constant current source 37, as connected, prevents a bias current through the paralleled transistors 36a of stage 34 from changing during the operation of the circuit. The field effect transistor 37 provides an excellent constant current supply as it has a very high output resistance with the drain voltage selected to lie within the operating range between pinch off and breakdown voltages. A change in the supply voltage, or a change in the load impedance, will change the drain current by only a very small amount as the result of the very low output conductance of such a device.

The constant current source will significantly improve the common mode rejection capability of the differential amplifier stage 34 and will further increase its thermal stability.

The output of the stage 34 is connected to a high gain amplifying stage 39, which is shown in the preferred construction including a pair of associated high gain micro-powered operational amplifier 40 and 41 which, in practice, can with stage 34 provide an amplification factor of the order of 5000. The amplifier 40 and 41 are similarly constructed with similar feedback capacitors 42 and 43 connecting the input-output terminals of an internal inverting stage, not shown, to establish a very low frequency response. The capacitors 42 and 43 function to create a roll-off of the upper frequency response of the amplifiers.

The amplifier 40 had the non-inverting input 44 connected to the output of the transistor stage 34. The second or inverting input 45 of amplifier 40 is connected in series with a resistor 46 to the output of amplifier 40 and to the common reference in series with a capacitor 47, a fixed resistor 48 and a gain controller resistor 49. The low frequency roll-off characteristic and particularly the lower half power frequency or $3db$ point is determined by this series RC impedance to the inverting terminal 45. A single polarity power supply operation is obtained from the amplifier output as a result of this series connection and the feedback resistor 46 connection to the output terminal.

The output of amplifier 40 is connected to the noninverting input of the second stage operational amplifier 41. The amplifier 41 includes a gain controlling feedback resistor 50 having a further paralleled capacitor 51 providing the additional frequency compensation. This network is connected to the inverting or negative input terminal and further reduces the amplifier's upper half power frequency of $edb$ point.

The inverting input of the amplifier 41 is also connected to the common reference by a capacitor 52 and a series resistor 53 to provide the negative bias supply and establish a single polarity power supply operation with the desired lower half power frequency point.

The cascaded operational amplifiers 40 and 41 provide low noise, high gain amplification which permits accurate and reliable detection of the small voltage changes associated with the environmental pollutant products such as that caused by combustion, air pollution and the like.

The output of the operational amplifier is an amplified signal directly related to the small input voltage signal to the dual field effect transistor unit 34. The stabilized and amplified output signal is connected by a DC coupling capacitor 54 to a suitable trigger unit for driving the alarm circuitry and, in particular, to activate the lamp 16 in the illustrated embodiment.

The illustrated alarm circuitry is responsive to a positive or negative voltage signal variation and includes a pair of programmable unijunction transistors 55 and 56 having inputs connected in common to a bias supply branch 57 and to the coupling capacitor 54 of the amplifier 41. The capacitor 54 provides DC isolation such that DC signals related to thermal variations at the amplifiers cannot trigger the alarm circuitry. Thus as a pollutant related signal moves from the quiescent operating point, it will tend to drive one transistor on and the ohter transistor off depending upon direction of movement.

More particularly, the one unijunction transistor 55 has its gate 58 supply connected to a bias supply branch 59, with its anode electrode 60 connected as an input to branch 57. The second unijunction transistor 56 has its gate 61 connected as an input and its anode electrode 62 connected to a bias supply branch 63. The cathode side of the programmable unijunctions 55 and 56 are connected in common to each other and to the bias supply through a suitable resistor 64 and also directly to the gate of a controlled rectifier 65 in series with a suitable current limiting resistor 66. The controlled rectifier 65 is connected in series with the lamp 16 and a reset switch 67 to the power supply. Thus, if either one of the programmable unijunction transistors 55 and 56 is turned on, a signal is applied to turn on the controlled rectifier 65 and thereby energize the lamp 16.

The transistor 56 is turned on by an increased positive voltage signal at line 57. The increased voltage applied to the anode of transistor 55 drives it off. If a negative voltage signal is transmitted, however, the anode voltage drop drive the transistor 55 on and thereby transmitts an output signal to the gate of the controlled rectifier 65.

A temperature stabilizing diode 68 is connected in the voltage dividing branch defining the gate supply 59 and particularly to the gate of transistor 55.

The bias supply branch 63 for the transistor 56 includes a temperature stabilizing transistor 69 connecting the anode 62 to the positive side of the bias supply. The transistor 69 in turn is controlled from a voltage dividing branch 70 which includes a temperature stabilizing diode unit 71, which may be a pair of series connected diodes similar to the diode 68. The diode unit 71 is connected between the base of the transistor and the negative side of the supply. The diodes 71 and transistor 69 provide further temperature stabilization to the operation of the unijunction transistors 55 and 56.

The programmable unijunction transistors 55 and 56 are excellent devices for the particular application as they have a very low leakage current and, consequently, create a minimal load on the bias supply circuit.

Thus, regardless of whether there is a negative or a positive voltage variation as a result of the change in the permittivity of the capacitor sensing means, one of the transistors 55 and 56 is driven on thereby providing for detection of both positive and negative variation from the normal environmental conditions.

In summary, the sensing unit is mounted with the capacitance unit exposed to the surrounding environment and with a normal environmental condition the output of the operational amplifier is in a quiescent condition. Transistors 55 and 56 are in a normal non-conducting standby condition. Products such as are generated within the surrounding environment in the incipient stage of combustion will rapidly move into the vicinity of the capacitance unit and particularly the special electrode. As a result of the adsorption and other interaction of the products with the electrode material 13, the charge gradient or permittivity of the capacitance unit changes, with a resulting change in the voltage or potential applied to the gate of the dual field effect transistor 36a. As the result of the very high input impedance of the circuit, very slight changes can be reliably detected.

Depending upon whether or not the change is a positive or negative variation in the capacitance, a corresponding voltage change will be applied to the amplifier stage 34. In either event, a related polarity change in conductivity is established with the resulting change in the signal to the positive input of the operational amplifier 40. A corresponding amplified change in the output of the amplifier 41 is impressed on the transistors 55 and 56 via the capacitor 54. As previously noted, either a positive of a negative deviation of a selected level triggers the controlled rectifier 65 to turn on lamp 16, or otherwise actuating any other suitable alarm or signalling means.

In this manner, a reliable environmental pollutant sensing device is provided.

The present invention thus provides an unusually sensitive detection system and particularly teaches a unique surface reaction electrode which interacts with the free space environment for determining the gaseous products in the surrounding atmosphere and is particularly adapted to determining incipient stages of combustion, air pollution and the like. The invention can be employed in any gaseous environment in which the products generated interact with at least one special electrode means to provide a change in the conductivity of the sensing unit. The illustrated structure provides a practical construction for employing an electrode in accordance with the special surface reactive layer. Any other suitable structure can be employed. Thus, the pair of capacitance electrode means may be similarly structured with the reactive layers and of course the special novel apertured shields or the preferred circuit is not essential. Thus, the novel structure and circuit is setforth to describe the best mode of carrying out the invention. In relatively large areas, a plurality of capacitive units may be distributed throughout the area and connected to a single processing circuit or to individual processing circuits.

Various modes of carrying out the invention are contemplated as being within the scope of the following claims particularly pointing out and distinctly claiming the subject matter which is regarded as the invention.

We claim:

1. An environmental gaseous product capacitance sensing apparatus for detecting the presence of environmental borne contaminating products, comprising a pair of spaced capacitance electrode means separated by an essentially non-conductive free space, a first of said electrode means comprised of a material having an oxidized surface layer less than 1000 microinches thick, said material being electrically conductive and forming a limited reactive layer in the surrounding environment, said surface layer reacting with said contaminating products to define a sensing electrode means.

2. An environmental gaseous product capacitance sensing apparatus for detecting the presence of environmental borne contaminating products, comprising a pair of spaced capacitance electrode means separated by an essentially non-conductive free space, a first of said electrode means including a surface of a corrosion resistant active material which is electrically conductive and forms a limited reactive layer in the surrounding environment, said material is selected from the group consisting of (a) the metals of Group VIII of the Periodic Table, (b) carbon, (c) copper and (d) alloys containing at least 5% by weight of said (a), (b) and (c).

3. The apparatus of claim 2 wherein said material is selected from period 4 of Group VIII metals of the Periodic Table.

4. The apparatus of claim 2 wherein said material is selected from period 5 of Group VIII metals of the Periodic Table.

5. The apparatus of claim 2 wherein said material is selected from period 6 of the Group VIII metals of the Periodic Table.

6. The apparatus of claim 1 wherein said material is selected from the group consisting of rhodium, ruthenium, platinum, palladium, osmium and iridium and alloys containing at least 5% of rhodium, ruthenium, platinum, palladium, osmium and iridium.

7. The apparatus of claim 1 wherein said material is a metal selected from a group consisting of rhodium, palladium and platinum and the alloys containing at least 5% of rhodium, palladium and platinum.

8. The apparatus of claim 1 wherein said material is selected from the class consisting of rhodium and an alloy containing at least 5% of rhodium.

9. The apparatus of claim 1 wherein said material is selected from the class consisting of palladium and an alloy containing at least 5% of palladium.

10. The apparatus of claim 1 wherein said material is selected from the class consisting of platinum and an alloy containing at least 5 % of platinum.

11. The apparatus of claim 1 wherein said material is selected from the class consisting of ruthenium and an alloy containing at least 5 % of ruthenium.

12. The apparatus of claim 1 wherein said material is stainless steel.

13. The apparatus of claim 1 wherein said sensing electrode means includes a plate-like base conductor, a gold strike applied to said conductor, and said material being selected from the platinum group metals and integrally plated to the gold strike and forming the active layer.

14. The apparatus of claim 1 wherein the second of said electrode means is a generally cup-shaped, perforated metal member, said sensing electrode means being located within said metal member, and means to ground said metal member to define an electrical shield about said sensing electrode means.

15. The apparatus of claim 14 including a second cup-shaped, perforated metal member mounted in telescoped, spaced relation to the first member and connected to said ground means.

16. The apparatus of claim 1 including second electrode means spaced from the sensing electrode means and connected to an enclosure surrounding the sensing electrode means, said second electrode means being grounded and being apertured to permit relatively free movement of the surrounding environment with the contaminating products into engagement with the active material of the sensing electrode means, a high bulk resistivity support within said enclosure and connected to said sensing electrode means to support the same, a high input impedance amplifying circuit means mounted within the enclosure and an electrical shield member within the enclosure overlying the support and circuit means.

17. An environmental gaseous product capacitance sensing apparatus for detecting the presence of environmental contaminating products, comprising an amplifying circuitry including a high impedance input means, a capacitance sensing means including a pair of spaced capacitance electrode means having a non-conductive free space therebetween, a first of said electrode means having a corrosion resistant conductive surface material selected from the group consisting of (a) the metals of Group VIII of the Periodic Table, (b) carbon, (c) copper and (d) alloys containing at least 5% by weight of (a), (b) and (c), said surface defining an active material which interacts with the contaminating products to change the electrical output of the capacitance means, and said amplifying circuitry having said high impedance input means connected to the capacitance sensing means to produce an amplified output of the capacitance sensing means.

18. The apparatus of claim 17 wherein a high impedance resistance means is connected in parallel with the capacitance sensing means to establish a large paralleled resistance preventing accumulation of charge thereon.

19. The apparatus of claim 18 wherein the resistance means is a Zener diode.

20. The apparatus of claim 17 wherein the second electrode means is a grounded conductive member surrounding the first electrode means and being apertured to permit relatively free movement of the surrounding environment between the electrode means and into engagement with said active material, the first electrode means being a disc-like element mounted within the second electrode means, a circuit board mounted within said enclosure, and a high surface and bulk resistivity insulator supporting said first electrode means on said circuit board.

21. The apparatus of claim 20 including a ground shield member mounted in telescoped overlying relationship to said circuit board within said enclosure.

22. The apparatus of claim 20 wherein a high impedance resistance means is connected in parallel with the capacitance sensing means to establish a large paralleled resistance preventing accumulation of charge thereon.

23. The apparatus of claim 17 wherein the amplifying circuitry includes a dual field effect transistor unit connected as a differential amplifier with a first gate connected to the sensing electrode to define the high input impedance and having a second gate, a constant current source connected as a bias supply to said transistor unit, an operational amplifier means having an input connected to the output means of the transistor unit to provide an amplified signal corresponding to the capacitance of the sensing means, and a detection circuit connected to the output of the operational amplifier and responsive to selected changes of negative and positive potential voltages from a quiescent operating voltage to indicate the corresponding selected change in the capacitance charge gradient.

24. The apparatus of claim 23 wherein said operational amplifier means includes a pair of cascaded operational amplifiers connected in a non-inverting circuit and having feedback means connecting the non-inverting inputs connected to the output of corresponding amplifier for bias to provide a single polarity power supply connection, said first operational amplifier having one input connected to the output of the transistor unit, said amplifiers having a capacitive feedback means to reduce the high frequency response and a resistive-capacitive input means to control the low frequency response.

25. The apparatus of claim 17 wherein said first electrode means is a disc-like plate having a threaded shaft secured to the center thereof, an enclosure having a front wall opening slightly greater in size than said electrode means, a perforated cupshaped ground shield connected to said enclosure in overlying relationship to said opening, a cup-shaped support member opening outwardly and located within the enclosure and in overlying relationship to the opening, a tubular insulator of a high surface and bulk resistivity insulating material secured within the center of the support member and having an opening to accommodate said threaded shaft, said insulator projecting outwardly of the support member and having a supporting flange, a contact nut located within said insulator and threadingly receiving said shaft, a circuit board having an opening telescoped over said insulator and resting on said flange, said amplifying circuitry including an amplifier means mounted on said circuit board, and having a high impedance input element connected to said contact nut, and an electrostatic shield member located within the enclosure and telescoped over said circuit board and support into abutting relation to the front wall to electrically shield said amplifier means and said contact, said shield member having a lead opening for accommodating electrical leads to said amplifier means.

* * * * *

UNITED STATES PATENT AND TRADEMARK OFFICE
CERTIFICATE OF CORRECTION

PATENT NO. : 3,989,463
DATED : November 2, 1976
INVENTOR(S) : CARL F. KLEIN ET AL It is certified that error appears in the above-identified patent and that said Letters Patent are hereby corrected as shown below:

Column 2, Line 58, after "free" cancel "ro" and insert --- or ---;

Column 4, Line 7, after "capacitance" cancel "meeans" and insert --- means ---;

Column 5, Line 60, after "combustion" cancel "sinsitivity" and insert --- sensitivity ---;

Column 8, Line 19, after "22" cancel "proejcts" and insert --- projects ---;

Column 10, Line 31, after "frequency" cancel "of edb" and insert --- or 3db ---;

Column 10, Line 60, after "the" cancel "ohter" and insert --- other ---;

Column 11, Line 13, after "55" cancel "drivesit" and insert --- drives it ---;

UNITED STATES PATENT OFFICE
CERTIFICATE OF CORRECTION

Patent No. 3,989,463  Dated November 2, 1976

Inventor(s) Carl F. Klein et al.

It is certified that error appears in the above-identified patent and that said Letters Patent are hereby corrected as shown below:

Column 12, line 2, after "positive" cancel "of" and insert --- or ---;

Column 16, line 1, after "board" cancel the comma ",";

Signed and Sealed this

Twenty-fourth Day of May 1977

[SEAL]

Attest:

RUTH C. MASON  
*Attesting Officer*

C. MARSHALL DANN  
*Commissioner of Patents and Trademarks*